(12) United States Patent
Millerd

(10) Patent No.: US 7,666,168 B2
(45) Date of Patent: Feb. 23, 2010

(54) SYRINGE GUARD WITH SELECTED NEEDLE CONFIGURATIONS

(76) Inventor: Don Millerd, 7960 Convoy Ct., San Diego, CA (US) 92111

( * ) Notice: Subject to any disclaimer, the term of this patent is extended or adjusted under 35 U.S.C. 154(b) by 840 days.

(21) Appl. No.: 11/055,415

(22) Filed: Feb. 10, 2005

(65) Prior Publication Data
US 2006/0111679 A1 May 25, 2006

Related U.S. Application Data

(63) Continuation-in-part of application No. 10/983,108, filed on Nov. 5, 2004, now Pat. No. 7,198,617.

(51) Int. Cl.
A61M 5/32 (2006.01)

(52) U.S. Cl. .................. 604/198; 604/192; 604/263; 604/110

(58) Field of Classification Search ................. 604/198, 604/193, 263, 110, 227, 192, 187
See application file for complete search history.

(56) References Cited

U.S. PATENT DOCUMENTS

| 4,425,120 A | 1/1984 | Sampson et al. |
| 4,664,654 A | 5/1987 | Strauss |
| 4,681,567 A | 7/1987 | Masters et al. |
| 4,781,692 A | 11/1988 | Jagger et al. |
| 4,894,055 A | 1/1990 | Sudnak |
| 4,911,693 A | 3/1990 | Paris |
| 5,037,402 A | 8/1991 | Bartman |
| 5,061,251 A | 10/1991 | Juhasz |
| 5,104,384 A | 4/1992 | Parry |
| 5,167,635 A | 12/1992 | Haber et al. |
| 5,167,640 A | 12/1992 | Balding |
| 5,176,656 A | 1/1993 | Bayless |
| 5,197,953 A | 3/1993 | Colonna |
| 5,222,945 A | 6/1993 | Basnight |
| 5,232,457 A | 8/1993 | Grim |
| 5,242,420 A | 9/1993 | Martin |
| 5,267,972 A | 12/1993 | Anderson |
| 5,267,977 A | 12/1993 | Feeney, Jr. |
| 5,279,566 A | 1/1994 | Kline, Jr. et al. |
| 5,292,314 A | 3/1994 | D'Alessio et al. |
| 5,295,975 A | 3/1994 | Lockwood, Jr. |
| 5,300,040 A | 4/1994 | Martin |
| 5,324,265 A | 6/1994 | Murray et al. |
| 5,346,480 A | 9/1994 | Hess et al. |
| 5,376,080 A | 12/1994 | Petrussa |
| 5,389,085 A | 2/1995 | D'Alessio et al. |

(Continued)

*Primary Examiner*—Kevin C Sirmons
*Assistant Examiner*—Phillip Gray
(74) *Attorney, Agent, or Firm*—Frost Brown Todd LLC

(57) ABSTRACT

A device for expelling a fluid through a needle mounted on a hub includes an elongated luer member that has a distal portion dimensioned to engage the needle hub to provide fluid communication between the luer member and the needle. An adapter anchors the luer member within the device. Slidingly mounted on the adapter is a cylindrical-shaped inverted plunger that is movable thereon between an advanced position and a withdrawn position. A needle guard is biased by a biasing member to extend distally from the luer member when the plunger is in the advanced position. The guard is selectively engageable with the plunger to be retracted to expose the distal portion of the luer member for fluid engagement with the needle hub when the plunger is moved to the withdrawn position.

19 Claims, 5 Drawing Sheets

U.S. PATENT DOCUMENTS

| | | |
|---|---|---|
| 5,403,286 A | 4/1995 | Lockwood, Jr. |
| 5,478,316 A | 12/1995 | Bitdinger et al. |
| 5,540,667 A | 7/1996 | Tanner, II |
| 5,582,597 A | 12/1996 | Brimhall et al. |
| 5,591,138 A | 1/1997 | Vaillancourt |
| 5,695,475 A | 12/1997 | Best, Jr. et al. |
| 5,713,871 A * | 2/1998 | Stock ........................ 604/192 |
| 6,162,197 A | 12/2000 | Mohammad |
| 6,379,336 B1 | 4/2002 | Asbaghi et al. |
| 6,530,905 B2 | 3/2003 | Asbaghi |

* cited by examiner

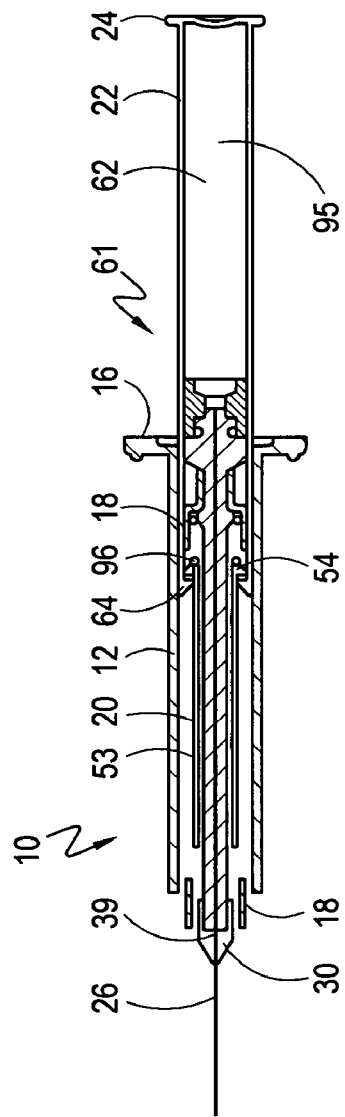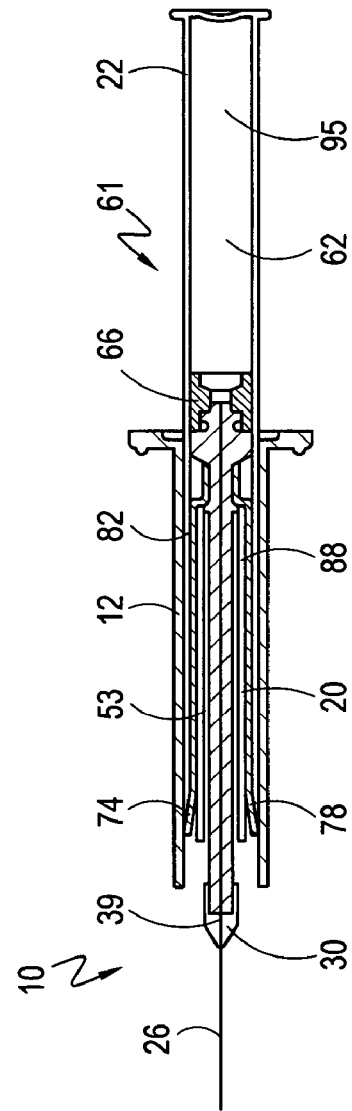
Fig. 3B
Fig. 4B

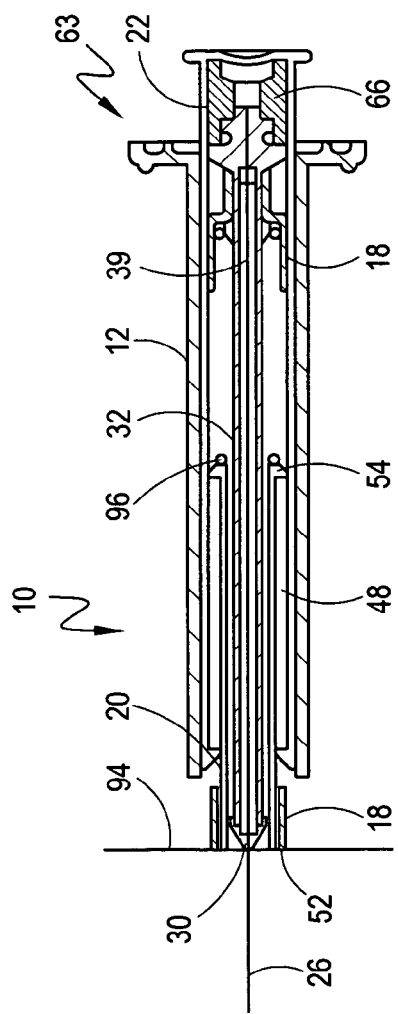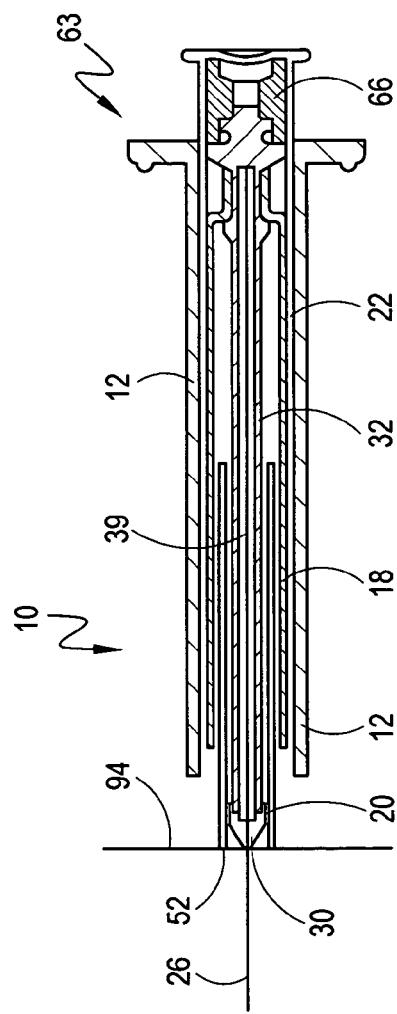

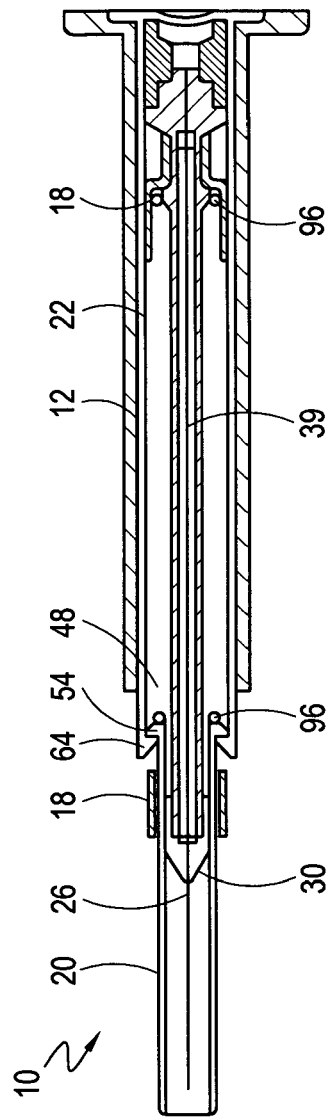
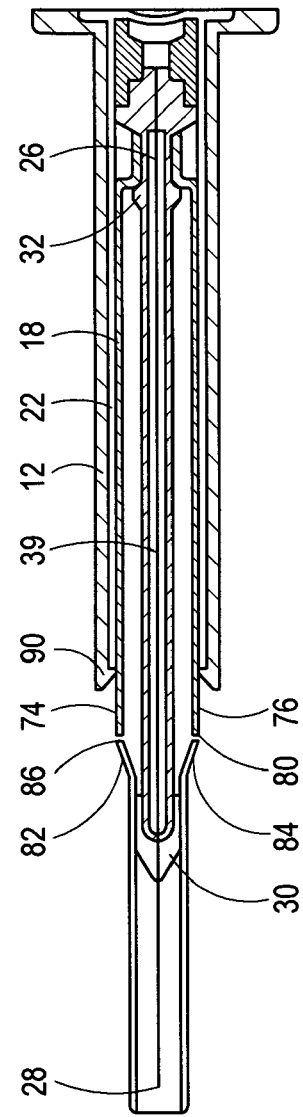
Fig. 3D
Fig. 4D

SYRINGE GUARD WITH SELECTED NEEDLE CONFIGURATIONS

This application is a continuation-in-part of application Ser. No. 10/983,108, filed Nov. 5, 2004 now U.S. Pat. No. 7,198,617, which is currently pending. The contents of application Ser. No. 10/983,108 are incorporated herein by reference.

FIELD OF THE INVENTION

The present invention pertains generally to devices for providing injections with needles. More particularly, the present invention pertains to protective devices for receiving needles prior to the administration of an injection. The present invention is particularly, but not exclusively, useful for passively covering and protecting the needle of an injection syringe after its use.

BACKGROUND OF THE INVENTION

Recent research from the Centers for Disease Control and Prevention (CDC) shows that approximately 384,000 needle sticks or similar injuries occur among health care workers in U.S. hospitals each year. Unfortunately, each accidental needle stick has the potential to expose a health care worker to a life-threatening virus such as hepatitis or HIV. In addition to the needle sticks that occur in hospitals, accidental needle sticks can also occur in other health care settings. For example, needle stick injuries can occur at clinics or during home health care. In fact, some studies have estimated that over 600,000 needle sticks occur in the U.S. each year, and approximately 1,000 of these accidental needle sticks result in a life-threatening infection.

For each accidental needle stick, health care providers are obligated to test and counsel the exposed worker. Further, follow-up testing for HIV must be conducted approximately six months after the exposure. It is to be appreciated that the costs associated with the testing, lab work, the worker's lost time, and the associated tracking and administrative costs, can be considerable.

Accidental needle sticks can occur in several ways. For example, sudden movement by the patient can cause a health care worker to lose control of a syringe, resulting in injury. Attempts to manually recap a needle following an injection can also result in injury. Moreover, injuries often result when contaminated, unprotected needles are left unattended or disposed of improperly. In addition to accidental needle sticks, unnecessary exposure to bloodborne pathogens can result when a health care worker mistakenly reuses a contaminated needle on a patient.

One particular type of syringe that is prone to needle stick injuries is the fillable injection syringe. In overview, these fillable injection syringes are designed to be filled with a medicament from a medicament vial by the same user that administers an injection. Heretofore, a typical procedure has involved removing a cap that covers the sharp needle tip of the fillable injection syringe. With the needle exposed, the needle tip is inserted into a vial containing medicament. This step generally occurs just prior to an injection. Next, the plunger is depressed to void the syringe chamber of air. With the syringe voided, the plunger is retracted to draw a specified quantity of medicament into the syringe chamber. Once the medicament has been loaded into the syringe, the needle is then inserted into a patient and the plunger is depressed to inject the medicament into the patient. After the injection, the needle is removed from the patient and often must be manually recapped to protect the contaminated needle. After recapping, it is often difficult to distinguish between used and unused syringes.

Fillable injection syringes and needles are often obtained separately. Typically, the syringes are available for use with different sized needles. This allows doctors to obtain and store fewer syringes. Then, when an injection is needed, a desired needle is simply mounted on a syringe.

In light of the above, it is an object of the present invention to provide a device that passively covers and protects a needle after first filling the device with medicament and then injecting the medicament into a patient. It is another object of the present invention to provide a device which guards the needle prior to an injection procedure and uses the same guard to passively guard the needle after an injection procedure. It is still another object of the present invention to provide a device in which the position of the needle guard is controlled and regulated by plunger movements that are required in a typical fill and inject procedure. It is yet another object of the present invention to provide a device having an integral mechanism that prevents reuse of the syringe (after use and contamination) by disabling the plunger at the completion of an injection procedure. Still another object of the present invention is to provide such a device for use with commercially available needles. Still another object of the invention is to provide a device with a needle guard that is movable to allow mounting of a needle on the device before use. Yet another object of the present invention is to provide a protective device for a medical syringe that is easy to use, relatively simple to implement, and comparatively cost effective.

SUMMARY OF THE INVENTION

A device for expelling a fluid, such as a medicament, through a hypodermic needle mounted on a hub includes an extended luer member that has a proximal portion, a distal portion and a fluid conduit extending along an axis therebetween. The distal portion of the extended luer member is dimensioned to engage the needle hub to provide fluid communication between the fluid conduit and the needle. When engaged, the needle extends away from the distal portion of the luer member to a sharp needle tip at its own distal end. Additionally, the device includes an adapter for anchoring the proximal portion of the luer member. The adapter includes a substantially cylindrical-shaped wall surrounding a cavity bounded by an open distal end and a proximal end substantially covered by a base. Slidingly mounted on the adapter is a cylindrical-shaped inverted plunger that is movable thereon between an advanced position and a withdrawn position. When the plunger is in the withdrawn position, a fluid chamber is created between the plunger and the adapter base. Specifically, the chamber is formed by a seal engaging the proximal portion of the luer member which is slidingly received by the plunger to form a fluid tight boundary for the fluid chamber. For the present invention, a tube-shaped needle guard having a lumen is biased by a biasing member such as a spring to extend distally from the distal portion of the luer member when the plunger is in the advanced position. The guard is selectively engageable with the plunger to be retracted into the adapter cavity and over the elongated luer member to expose the distal portion of the luer member for fluid engagement with the needle hub when the plunger is moved to the withdrawn position.

In greater structural detail, the luer member includes a head section that engages the adapter. The head section is connected to a shaft section which extends distally from the head section along the axis to a shaft end that is spaced from the head section by a shaft length that is at least as long as the length of the adapter. Therefore, the luer member extends through the cavity and the open distal end of the adapter. As the extremity of the distal portion of the luer member, the shaft end is dimensioned for engagement with the needle hub. Engagement between the needle hub and shaft end may be achieved through a number of known methods. For instance, the needle hub may include a circumferential protrusion that fits into a corresponding circular groove on the shaft end. Alternatively, the needle hub may include male or female threadings to allow the hub to be screwed into reciprocal threadings on the shaft end. Or, more simply, the needle hub may be slipped snugly onto the shaft end.

As described in greater detail below, a mechanism provides selective engagement between the plunger and guard during the course of an injection procedure. More specifically, the plunger movements that are required to expose the distal portion of the extended luer member for mounting a needle thereon, to fill the fluid chamber, and to dispense a fluid from the fluid chamber also function to control the position of the guard. In functional overview, prior to an injection procedure, the guard is locked in an extended position distal of the luer member and can only be unlocked by a movement of the plunger. Once unlocked, the guard can be retracted to expose the distal portion of the luer member. This allows the needle hub to be mounted on the distal portion of the luer member, and in addition, allows the needle to be inserted into a medicament vial to fill the fluid chamber and to be inserted into a patient for an injection. When the plunger is withdrawn proximally relative to the adapter to create the fluid chamber, the plunger and guard engage one another, and the guard moves proximally to expose the distal portion of the luer member and a needle mounted thereon. On the other hand, when the plunger is advanced (i.e. moved distally), the plunger releases the guard. Once released, the guard is free to move distally under the influence of the spring. As a consequence of this interaction, after the plunger is depressed to complete an injection, the guard is released and allowed to move distally to its extended position to cover and protect the needle.

In operation, the plunger is initially located in an advanced position relative to the adapter. Next, the plunger is withdrawn proximally which causes the plunger to engage the guard and to move the guard proximally with the plunger to a retracted position. With the guard retracted, the next step is to mount the needle hub onto the exposed shaft end of the luer member. Then the distal tip of the needle may be inserted into a medicament vial. At this point, the plunger can be depressed to expel air into the vial and void the fluid chamber. During plunger advancement, the plunger operatively disengages the guard. Thus, distal movement of the guard is only prevented by the contact between the guard and the vial. Next, the plunger can be withdrawn to fill the fluid chamber with medicament. During this plunger withdrawal, the plunger again engages and retracts the guard. Thus, when the needle is removed from the vial, the distal tip of the needle remains unguarded and exposed. The syringe is now ready for an injection.

To inject a medicament into a patient, the distal tip of the needle is inserted into the patient and the plunger depressed. This distal advancement of the plunger releases the guard. Once released, the guard is free to move distally under the influence of the spring. Thus, as the needle is withdrawn from the patient, the needle retracts proximally into the guard, which remains in contact with the patient's skin. Once the syringe has been removed from the patient, the plunger and adapter can be advanced distally relative to the syringe body to lock the guard in place.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3B is a sectional view of the syringe as in FIG. 3A, shown after a plunger movement has unlocked and distally retracted the guard;

FIG. 3C is a sectional view of the syringe as in FIG. 3A, shown after the needle's distal tip has been inserted into an object (i.e. medicament vial or patient) and thereafter the plunger has been advanced proximally;

FIG. 3D is a sectional view of the syringe as in FIG. 3A, shown after the plunger and adapter have been advanced distally relative to the syringe body to lock the guard in position and prevent inadvertent reuse of the syringe;

FIG. 4B is a sectional view of the syringe as in FIG. 3A, shown after a plunger movement has unlocked and distally retracted the guard;

FIG. 4C is a sectional view of the syringe as in FIG. 3A, shown after the needle's distal tip has been inserted into an object (i.e. medicament vial or patient) and thereafter the plunger has been advanced proximally; and FIG. 4D is a sectional view of the syringe as in FIG. 3A, shown after the plunger and adapter have been advanced distally relative to the syringe body to lock the guard in position and prevent inadvertent reuse of the syringe.

DESCRIPTION OF THE PREFERRED EMBODIMENTS

Figure 1:
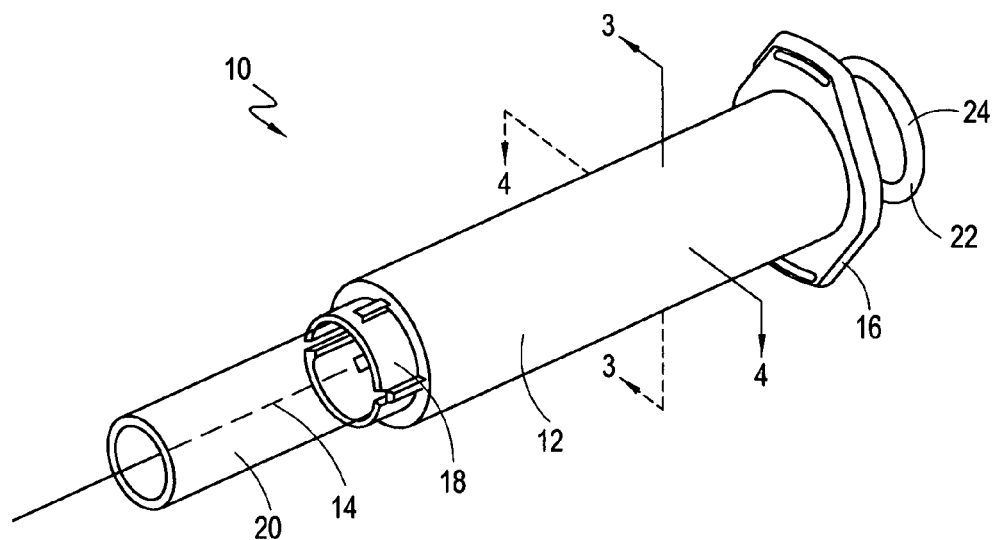
FIG. 1 is a perspective view of a device for expelling a fluid through a hypodermic needle mounted on a hub, shown in its initial configuration.

Referring initially to FIG. 1, a syringe device for expelling a fluid through a needle mounted on a hub is shown and generally designated 10. As shown in FIG. 1, the device 10 includes a substantially cylindrical syringe body 12 that is centered on an axis 14 and formed with a finger grip 16 at its proximal end. FIG. 1 further shows that the device 10 includes an adapter 18 sized to fit within the syringe body 12. The adapter 18 includes a cylindrical portion that is also centered on the axis 14. For the device 10, a substantially cylindrical needle guard 20 is provided and positioned co-axially with both the syringe body 12 and adapter 18. The guard 20 is sized to fit within the adapter 18. It can be further seen that the device 10 includes a plunger 22 that is formed with a grip flange 24 at its proximal end.

Figure 2:
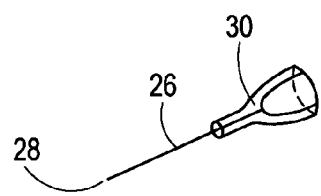
FIG. 2 is a perspective view of a hypodermic needle mounted on a hub for use with the device of FIG. 1.
Figure 3A:
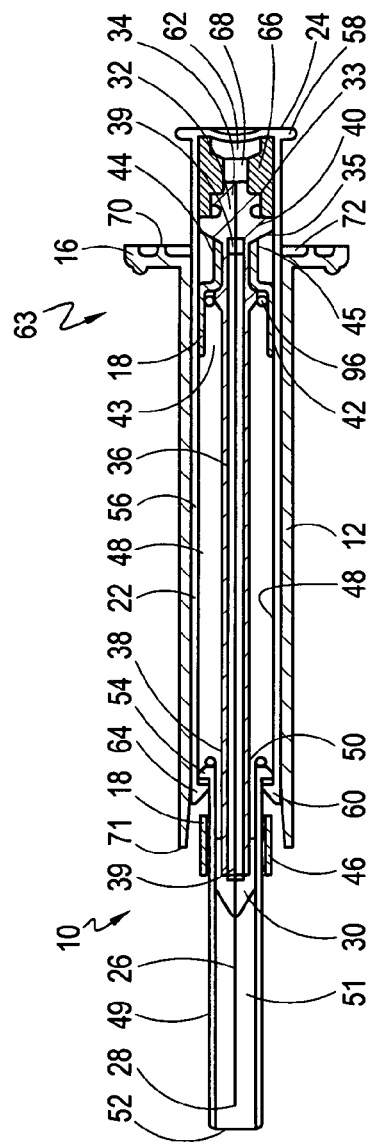
FIG. 3A is a sectional view of the syringe as seen along line 3-3 in FIG. 1, shown after a needle has been mounted on the luer member and with the guard locked over the needle's distal tip.

Referring to FIG. 2, a straight, elongated hypodermic needle 26 is shown extending from a sharp needle tip 28 to a needle hub 30. As best seen in FIG. 3A, the needle 26 may be mounted to the passively guarded, fillable injection device 10. Specifically, the device 10 includes a luer member 32 that receives and engages the needle hub 30. The luer member 32 has a proximal portion or head 34. Extending distally from the head 34 is a substantially cylindrical shaft 36 centered on the axis 14. The needle hub 30 is mounted to the luer member 32 at the shaft's distal portion or distal shaft end 38. Additionally, the head 34 has a proximal side 33 and a distal side 35 that engages the adapter 18. Circumferentially-spaced truss-like webs 40 are provided on the luer member 32 to reinforce the connection between the shaft 36 and the head 34. Furthermore, the luer member 32 includes a pipe-like conduit 39 that extends from the proximal side 33 of the head 34 to the shaft end 38. When the needle hub 30 is frictionally mounted on the shaft end 38, the needle hub 30 and luer member 32 are sealed together to establish fluid communication between the needle 26 and the conduit 39.

As shown in FIG. 3A, the adapter 18 engages the luer member 32 about the webs 40 thereby preventing rotational movement therebetween. The adapter 18 includes a substantially cylindrical wall 42 that is centered on the axis 14 and forms a cavity 43. The wall 42 extends from a proximal end 44 substantially covered by a base 45 to an open distal end 46. At its proximal end 44, the adapter 18 has a narrow circumference and is designed to engage the distal side 35 of the head 34 of the luer member 32. At its distal end 46, the adapter 18 has a broad circumference and is designed to engage the plunger 22 and receive the guard 20. As can be seen in FIG. 3A, the adapter 18 also includes two oppositely positioned, axially aligned slits 48.

As best seen in FIG. 3A, the adapter 18 is sized to allow the cylindrical guard 20 to move along the axis 14 into and out of the adapter cavity 43. Specifically, the guard 20 may be moved between an extended position 49 (shown in FIGS. 3A and 4A) to a retracted position 53 (shown in FIGS. 3B and 4B). Structurally, the guard 20 is a shell forming a lumen 51 that extends between an open proximal end 50 and an open distal end 52. The guard 20 includes abutments 54 that extend radially outward from the proximal end 50.

Also in FIG. 3A, it can be seen that the inverted plunger 22 has a substantially cylindrical side member 56 that extends from a closed proximal plate member 58 to an open distal edge 60. Structurally, the cylindrical side member 56 surrounds a fluid chamber 62 and is slidingly mounted on the proximal end 44 of the adapter 18. FIG. 3A further shows that the plunger 22 is formed with tangs 64 that extend radially inward (i.e. toward the axis 14) and distally from the cylindrical side member 56 of the plunger 22.

It can be seen in FIG. 3A, that the device 10 includes an elastomeric seal 66 that is attached onto the proximal end 34 of the luer member 32. Specifically, the seal 66 is press fitted onto the proximal end 34 of the luer member 32. As shown, the seal 66 has a generally fusiform or spindle-like shape and is formed with a through-hole 68. When the open distal edge 60 of the plunger 22 is slid over the luer member 32 and adapter 18, the seal 66 compresses between the luer member 32 and the cylindrical side member 56 of the plunger 22 to establish sealed fluid communication between the fluid chamber 62 and the conduit 39 of the luer member 32. When the needle hub 30 is mounted on the luer member 32 to establish fluid communication between the needle 26 and the conduit 39, the plunger 22 can be moved to a withdrawn position 61 (shown in FIGS. 3B and 4B) to draw fluid through the needle 26 and into the chamber 62. Furthermore, the plunger 22 can be moved to an advanced position 63 (shown in FIGS. 3C and 4C) to expel fluid from the chamber 62 through the needle tip 28.

As further shown in FIG. 3A, the syringe body 12 extends from an open proximal end 70 to an open distal end 71. Positioned at the proximal end 70, the finger grip 16 includes a recess 72 sized to receive the grip flange 24 of the plunger 22. Functionally, the plunger 22 can be advanced distally after an injection until the grip flange 24 is positioned in the recess 72. Once the grip flange 24 is positioned in the recess 72 it cannot be removed; therefore, subsequent movement of the plunger 22 relative to the syringe body 12 is effectively prevented.

Figure 4A:
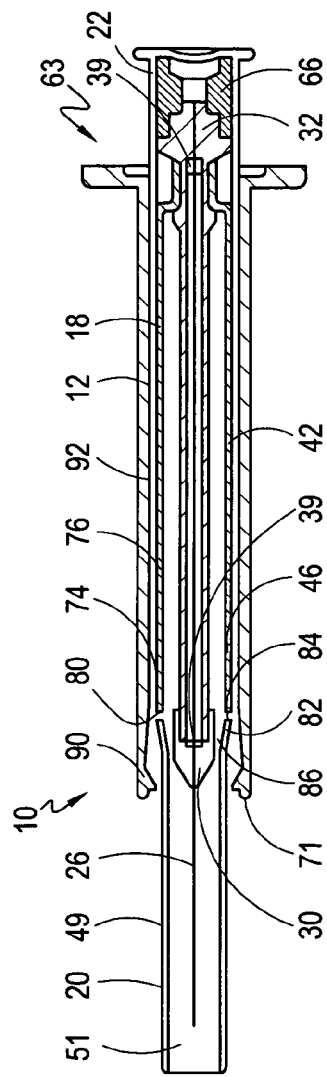
FIG. 4A is a sectional view of the syringe as seen along line 4-4 in FIG. 1, shown after a needle has been mounted on the luer member and with the guard locked over the needle's distal tip.

Turning to FIG. 4A, other features of the device 10 may be seen. Specifically, the adapter 18 is shown having cam levers 74 positioned at its distal end 46. The cam levers 74 are in a biased position 76 in which the plunger 22 forces them to be coincident with the rest of the cylindrical wall 42. However, the cam levers 74 mechanically prefer a relaxed position 78 (shown in FIG. 4B) in which the distal ends 80 of the cam lever 74 extend radially outward from the cylindrical wall 42.

As shown in FIG. 4A, the guard 20 has hinges 82. Similar to the cam levers 74 of the adapter 18, the hinges 82 of the guard 20 have a relaxed position 84 in which the proximal ends 86 of the hinges 82 extend radially outward from the rest of the guard 20. The biased position 88 of the hinges 82 is shown in FIG. 4B.

As further shown in FIG. 4A, the syringe body 12 can also include flanges 90 at its distal end 71. The flanges 90 extend distally and radially inward from the cylindrical portion 92 of the syringe body 12. Their purpose is discussed below.

By cross-referencing FIGS. 3A-D and 4A-D, it can be seen that the device 10 includes a mechanism to lock the guard 20 in an extended position 49 covering the needle tip 28 prior to an injection procedure. Once locked, the guard 20 can only be unlocked by movement of the plunger 22. As previously discussed, the adapter 18 is formed with cam levers 74 having distal lever ends 80. Comparing FIG. 4A with FIG. 4B, it can be seen that the cam levers 74 are deflectable by the cylindrical side member 56 of the plunger 22 from a relaxed position 78 (FIG. 4B) to a biased position 76 (FIG. 4A). In the relaxed position 78 (FIG. 4B), the cam levers 74 extend radially outward from the remaining cylindrical section of the adapter 18. On the other hand, as shown in FIG. 3A, in the biased (i.e. deflected) position 76, the cam levers 74 are coincident with the remaining cylindrical wall 42 of the adapter 18. When the plunger 22 is in the advanced position 63 shown in FIG. 4A, the cylindrical side member 56 of the plunger 22 contacts the cam levers 74 and deflects them into the biased position 76. As shown in FIG. 4A, when the cam levers 74 are in the biased position 76, the lever ends 80 engage the proximal ends 86 of the hinges 82 of the guard 20 and prevents proximal movement of the guard 20. When the plunger 22 is in its withdrawn position 61 as shown in FIGS. 3B and 4B, the cam lever 74 relaxes into its undeflected, outward position 78 (as shown in FIG. 4B) and allows the guard 20 to move proximally.

As an additional locking mechanism, the syringe body 12 may be moved relative to the adapter 18 to deflect the cam levers 74 of the adapter 18 with its flanges 90. As shown in FIG. 4D, the flanges 90 are moved toward the adapter 18 when the plunger 22 and adapter 18 are fully pushed into the syringe body 12. As a result, the flanges 90 contact and force the cam levers 74 of the adapter 18 to the biased position 76 to lock the device 10 to prevent any further proximal movement of the needle guard 20. This prevents inadvertent reuse of the device 10.

Operation

Initially, the device 10 is provided without a needle 26. To mount a needle 26 on the device 10, the needle guard 20 is first moved to the retracted position 53 by withdrawing the plunger 22. Then the needle hub 30 is frictionally engaged with the shaft end 38 of the luer member 32 as can be understood from FIGS. 3B and 4B. After mounting the needle hub 30 on the shaft end 38, the needle guard 20 is allowed to move to its extended position 49 to cover the needle 26 by moving the plunger 22 to its advanced position 63 as shown in FIG. 3A. As further shown in FIG. 3A the tangs 64 of the plunger 22 extend through the slits 48 in the adapter 18 to engage the abutments 54 and retract the guard 20 when the plunger 22 is withdrawn.

From FIG. 4A, it can be seen that the cylindrical side member 56 of the plunger 22 holds the cam levers 74 deflected inward to lock the guard 20 and prevent proximal movement of the guard 20. As illustrated by FIGS. 3A-B and 4A-B, use of the device 10 begins by withdrawing the plunger 22. Such proximal movement of the plunger 22 has several effects. Specifically, as shown in FIGS. 4A and 4B, initial proximal movement of the plunger 22 allows the cam levers 74 to relax outwardly from the axis 14 and unlock the guard 20 for proximal movement. As shown in FIGS. 3A and 3B, additional proximal movement of the plunger 22 engages the tangs 64 with the abutments 54, causing the guard 20 to be retracted with the plunger 22. Also, withdrawal of the plunger 22 draws air (or other fluid) through the needle 26 and into the fluid chamber 62.

Once the guard 20 has been retracted as shown in FIGS. 3B and 4B, the next step is to insert the exposed distal needle tip 28 into a medicament vial (illustrated by surface 94 in FIGS. 3C and 4C). At this point, the plunger 22 can be depressed as shown in FIGS. 3C and 4C to expel air into the vial and void the fluid chamber 62. Comparing FIGS. 3B and 4B with FIGS. 3C and 4C, it can be seen that during its advance the plunger 22 disengages the guard 20. Thus, as illustrated by FIGS. 3C and 4C, after advancing the plunger 22, distal movement of the guard 20 is only prevented by the contact between the distal end 52 of the guard 20 and the surface 94. Next, the plunger 22 can be withdrawn to fill the chamber 62 with medicament fluid 95 (note FIGS. 3B and 4B are representative of the configuration of the device 10 after the chamber 62 is filled with medicament 95). From FIG. 3B, it can be seen that during withdrawal of the plunger 22, the tangs 64 reengage the abutments 54. The result is that the plunger 22 engages the guard 20 and prevents distal advancement of the guard 20. As illustrated by FIGS. 3B and 4B, when the needle 26 is removed from the vial, the distal tip 28 of the needle 26 remains unguarded and exposed. The device 10 is now ready for an injection.

As illustrated by FIGS. 3C and 4C, to inject a medicament into a patient, the distal tip 28 of the needle 26 is inserted into the patient (represented by surface 94) and the plunger 22 is depressed. As shown in FIG. 3C, the distal advancement of the plunger 22 releases the guard 20. Once released, the guard 20 is free to move distally under the influence of a coil spring 96 that is interposed between the guard 20 and the adapter 18. Thus, as the needle 26 is withdrawn from the patient, the needle 26 retracts proximally into the guard 20 which remains in contact with the patient's skin (represented by surface 94). FIGS. 3A and 4A are representative of the device 10 after the needle 26 has been withdrawn from the patient and the needle 26 has passively retracted into the guard 20.

Once the device 10 has been removed from the patient, the plunger 22 and the adapter 18 can be advanced distally relative to the syringe body 12 to lock the guard 20 in place (FIG. 4D). FIGS. 3D and 4D also show that this places the grip flange 24 of the plunger 22 in the recess 72 formed in the syringe body 12. Functionally, once the device 10 is in the configuration shown in FIGS. 3D and 4D, the plunger 22 is disabled and the guard 20 completely covers the hollow needle 26 to protect the user from unwanted needle sticks and prevents inadvertent reuse of the device 10.

While the particular devices and methods as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A device for expelling a fluid through a hypodermic needle mounted on a hub, the device comprising:
   an adapter having a cylindrical-shaped wall surrounding a cavity, wherein the adapter defines an axis and has an open distal end and a proximal end substantially covered by a base;
   an elongated luer member having a proximal portion and a distal portion with a fluid conduit extending therebetween, wherein the proximal portion of the luer member is affixed to the adapter base to extend the luer member along the axis and through the adapter cavity to position the distal portion of the luer member proximate the distal end of the adapter;
   a cylindrical-shaped plunger positioned over the adapter and movable thereon between an advanced position and a withdrawn position to create a fluid chamber between the plunger and the adapter base when the plunger is in the withdrawn position;
   a tube-shaped guard having a lumen, wherein the guard is biased to extend distally from the distal portion of the luer member when the plunger is in the advanced position, and wherein the guard is selectively engageable with the plunger to be retracted into the adapter cavity and over the elongated luer member to expose the distal portion of the luer member for fluid engagement with the needle hub when the plunger is moved to the withdrawn position to create the fluid chamber and for subsequently expelling the fluid from the fluid chamber and through the needle; and
   a syringe body slidingly mounted on the adapter for relative axial movement thereon, the syringe body having a locking mechanism for locking the guard in an extended position to prevent reuse of the device.

2. A device as recited in claim 1 further comprising a biasing member positioned between the adapter and the guard, the biasing member biasing the guard to extend distally from the distal portion of the luer member when the plunger is in the advanced position.

3. A device as recited in claim 1 further comprising a seal which engages the proximal portion of the luer member and is slidingly received by the plunger to form a fluid tight boundary for the fluid chamber.

4. A device as recited in claim 1 wherein the adapter includes a cam lever for selectively engaging the guard to prevent unintended retraction of the guard, the cam lever disengaging the guard when the plunger is withdrawn.

5. A device as recited in claim 1 wherein the adapter includes an axially extending slit, the device further comprising a tang extending radially inward from the plunger and into the slit to engage the guard and to retract the guard into the adapter cavity and over the elongated luer member to expose the distal portion of the luer member for fluid engagement with the needle hub when the plunger is moved to the withdrawn position.

6. A device as recited in claim 5 further comprising an abutment extending radially outward from the guard to engage the tang when the plunger is moved to the withdrawn position.

7. A device for expelling a fluid from a fluid chamber through a needle mounted on a hub, the device comprising:
- an adapter defining an axis and having an adapter length along the axis, wherein the adapter comprises an axially extending slit, and a cylindrical-shaped wall surrounding a cavity;
- a luer member having a head section engaging the adapter, the head section connected to a shaft section, the shaft section extending distally from the head section along the axis to a shaft end, the shaft end being spaced from the head section by a shaft length at least as long as the adapter length, the shaft end being dimensioned for connection to the needle hub, said luer member having a conduit extending between the head section and the shaft end, wherein the conduit establishes fluid communication between the fluid chamber and the needle when the needle hub is mounted on the shaft end of said luer member;
- a guard for selectively protecting the needle when the needle hub is mounted on the shaft end of said luer member, the guard being movable along the axis with respect to the adapter;
- a plunger mounted for axial movement on the adapter, wherein proximal movement of the plunger withdraws the guard with respect to the adapter and establishes the fluid chamber within the plunger, and wherein distal movement of the plunger expels the fluid from the fluid chamber; and
- a tang extending radially inward from the plunger and into the slit to engage the guard and to retract the guard into the adapter cavity and over the luer member to expose the shaft end of the luer member for fluid engagement with the needle hub when the plunger is moved to the withdrawn position.

8. A device as recited in claim 7 wherein the plunger is movable between an advanced position and a withdrawn position, and wherein the guard is biased to extend distally from the shaft end of the luer member when the plunger is in the advanced position.

9. A device as recited in claim 8 further comprising a biasing member positioned between the guard and the adapter to bias the guard to extend distally from the shaft end of the luer member when the plunger is in the advanced position.

10. A device as recited in claim 9 wherein the adapter further comprises a base connected to the wall, the wall being substantially cylindrical and extending distally along the axis from the base to form the cavity, the base forming a channel in fluid communication with the cavity, and wherein the shaft section of the luer member extends distally from the head section of the luer member through the channel and the cavity of the adapter when the luer member engages the adapter.

11. A device as recited in claim 10 wherein the head section of the luer member has a proximal side and a distal side with the distal side engaging the adapter, the shaft section of the luer member extending distally from the distal side of the head section, and the conduit extending between the proximal side of the head section and the shaft end.

12. A device as recited in claim 11 wherein the guard comprises a substantially cylindrical shell forming a lumen, the guard being movable from an extended position in which the shaft end of the luer member is covered by the guard to a retracted position in which the shaft end is exposed.

13. A device as recited in claim 12 wherein the plunger comprises a proximal plate member and a substantially cylindrical side member extending distally from the plate member to an open distal edge for receiving the adapter.

14. A device for expelling a fluid through a hypodermic needle mounted on a hub, the device comprising:
- an adapter having a cylindrical-shaped wall surrounding a cavity, wherein the adapter defines an axis and has an open distal end and a proximal end substantially covered by a base, wherein the adapter comprises an axially extending slit;
- an elongated luer member having a proximal portion and a distal portion with a fluid conduit extending therebetween, wherein the proximal portion of the luer member is affixed to the adapter base to extend the luer member along the axis and through the adapter cavity to position the distal portion of the luer member proximate the distal end of the adapter;
- a cylindrical-shaped plunger positioned over the adapter and movable thereon between an advanced position and a withdrawn position to create a fluid chamber between the plunger and the adapter base when the plunger is in the withdrawn position;
- a tube-shaped guard having a lumen, wherein the guard is biased to extend distally from the distal portion of the luer member when the plunger is in the advanced position, and wherein the guard is selectively engageable with the plunger to be retracted into the adapter cavity and over the elongated luer member to expose the distal portion of the luer member for fluid engagement with the needle hub when the plunger is moved to the withdrawn position to create the fluid chamber and for subsequently expelling the fluid from the fluid chamber and through the needle;
- a tang extending radially inward from the plunger and into the slit to engage the guard and to retract the guard into the adapter cavity and over the elongated luer member to expose the distal portion of the luer member for fluid engagement with the needle hub when the plunger is moved to the withdrawn position; and
- an abutment extending radially outward from the guard to engage the tang when the plunger is moved to the withdrawn position.

15. A device as recited in claim 14 further comprising a biasing member positioned between the adapter and the guard, the biasing member biasing the guard to extend distally from the distal portion of the luer member when the plunger is in the advanced position.

16. A device as recited in claim 14 further comprising a seal which engages the proximal portion of the luer member and is slidingly received by the plunger to form a fluid tight boundary for the fluid chamber.

17. A device as recited in claim 14 wherein the adapter includes a cam lever for selectively engaging the guard to prevent unintended retraction of the guard, the cam lever disengaging the guard when the plunger is withdrawn.

18. A device as recited in claim 14 wherein the plunger comprises a proximal plate member and a substantially cylindrical side member extending distally from the plate member to an open distal edge for receiving the adapter.

19. A device as recited in claim 14 wherein the proximal portion of the luer comprises a head portion, where the head portion is connected to a shaft portion leading to a shaft end, wherein the distal portion comprises the shaft end.

* * * * *